US010357204B2

(12) United States Patent
Kuramoto

(10) Patent No.: US 10,357,204 B2
(45) Date of Patent: Jul. 23, 2019

(54) ENDOSCOPE SYSTEM AND OPERATING METHOD THEREOF

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 1399 days.

(21) Appl. No.: 14/339,672

(22) Filed: Jul. 24, 2014

(65) Prior Publication Data

US 2015/0094537 A1 Apr. 2, 2015

(30) Foreign Application Priority Data

Sep. 27, 2013 (JP) ................ 2013-202556

(51) Int. Cl.
*A61B 1/04* (2006.01)
*A61B 5/00* (2006.01)
*A61B 1/00* (2006.01)
*A61B 1/06* (2006.01)

(52) U.S. Cl.
CPC ........ *A61B 5/7271* (2013.01); *A61B 1/00009* (2013.01); *A61B 1/00057* (2013.01); *A61B 1/0638* (2013.01)

(58) Field of Classification Search
CPC ........... H04N 5/235; H04N 2005/2255; H04N 2209/049; A61M 2005/1726; A61B 1/00009; A61B 1/00057; A61B 1/0638; A61B 10/04; A61B 5/7271
See application file for complete search history.

(56) References Cited

U.S. PATENT DOCUMENTS 8,531,512 B2 9/2013 Gono et al.
2003/0176768 A1* 9/2003 Gono ................... A61B 1/0638
600/109

(Continued)

OTHER PUBLICATIONS

Japanese Office Action and English translation, dated May 31, 2017, for corresponding Japanese Application No. 2016-177437.

*Primary Examiner* — John P Leubecker
*Assistant Examiner* — Shankar Raj Ghimire
(74) *Attorney, Agent, or Firm* — Birch, Stewart, Kolasch & Birch, LLP

(57) ABSTRACT

A light source device simultaneously produces violet narrowband light and green narrowband light. A complementary color type imaging device of a complementary color type endoscope outputs first to fourth mixed pixel signals. In a complementary color second processor, a matrix operation unit performs a matrix operation of the first to fourth mixed pixel signals, and produces first and second display signals D1 and D2. A mixed color corrector corrects the first and second display signals D1 and D2 on the basis of relational expressions of "$D1'=D1-K_2 \times D2$" and "$D2'=D2-K_1 \times D1$". $K_1$ represents the ratio of a signal value of the second display signal to a signal value of the first display signal under independent application of only the violet narrowband light. $K_2$ represents the ratio of a signal value of the first display signal to a signal value of the second display signal under independent application of only the green narrowband light.

13 Claims, 11 Drawing Sheets

(56) References Cited

U.S. PATENT DOCUMENTS

| | | | |
|---|---|---|---|
| 2007/0102623 A1* | 5/2007 | Fengler | A61B 1/00009 250/208.1 |
| 2008/0306338 A1* | 12/2008 | Yamazaki | A61B 1/00009 600/109 |
| 2009/0058999 A1* | 3/2009 | Gono | A61B 1/00009 348/71 |
| 2009/0066787 A1* | 3/2009 | Yamazaki | A61B 1/0638 348/70 |
| 2009/0141125 A1* | 6/2009 | Yamazaki | A61B 1/0638 348/70 |
| 2009/0251532 A1* | 10/2009 | Abe | A61B 1/045 348/71 |
| 2009/0295939 A1* | 12/2009 | Abe | G06T 3/4015 348/223.1 |
| 2009/0295950 A1* | 12/2009 | Abe | H04N 9/045 348/241 |
| 2010/0032546 A1* | 2/2010 | Kawano | A61B 1/041 250/205 |
| 2010/0182414 A1* | 7/2010 | Suzuki | H04N 9/74 348/71 |
| 2012/0088969 A1* | 4/2012 | Takahira | A61B 1/00009 600/109 |
| 2012/0127292 A1* | 5/2012 | Yamazaki | A61B 1/00009 348/68 |
| 2012/0127293 A1* | 5/2012 | Yamazaki | A61B 1/00009 348/71 |
| 2013/0053703 A1* | 2/2013 | Yamamoto | A61B 1/0638 600/476 |
| 2013/0172675 A1* | 7/2013 | Yamazaki | H04N 9/643 600/109 |
| 2013/0265401 A1* | 10/2013 | Igarashi | A61B 1/0661 348/68 |
| 2013/0286175 A1* | 10/2013 | Hashimoto | A61B 1/0638 348/68 |
| 2013/0317371 A1* | 11/2013 | Takei | A61B 1/063 600/476 |
| 2013/0324797 A1* | 12/2013 | Igarashi | A61B 1/06 600/109 |
| 2014/0100427 A1 | 4/2014 | Saito et al. | |

* cited by examiner

ENDOSCOPE SYSTEM AND OPERATING METHOD THEREOF

CROSS-REFERENCE TO RELATED APPLICATIONS

The present application claims priority under 35 U.S.C. § 119 to Japanese Patent Application No. 2013-202556 filed on Sep. 27, 2013. The above application is hereby expressly incorporated by reference, in its entirety, into the present application.

BACKGROUND OF THE INVENTION

1. Field of the Invention

The present invention relates to an endoscope system that allows narrowband light observation and an operating method of the endoscope system.

2. Description Related to the Prior Art

In a recent medical field, diagnosis and treatment using an endoscope system, having a light source device, an electronic endoscope, and a processor device, are widely performed. The light source device produces illumination light and applies the illumination light to the inside of a human body cavity. The electronic endoscope images the inside of the body cavity irradiated with the illumination light by an imaging device, and produces an imaging signal. The processor device applies image processing to the imaging signal produced by the electronic endoscope to produce an observation image to be displayed on a monitor.

As an observation method used in the endoscope system, there is known narrowband light observation using special light (narrowband light) having a narrow wavelength band as the illumination light, in addition to normal light observation using normal light (white light) having a wide wavelength band as the illumination light. The narrowband light observation, for example, can improve visibility of a blood vessel pattern in a superficial layer of a mucosa membrane, though the blood vessel pattern is easily buried in optical information obtained under irradiation with the white light. Therefore, the narrowband light observation allows focusing attention on superficial blood vessels of the blood vessel pattern, and diagnosing the stage of a disease, the depth of a lesion, and the like from the state of the superficial blood vessels.

The narrowband light observation uses two types of narrowband light absorbable by hemoglobin in blood, that is, blue narrowband light having a center wavelength in the vicinity of 415 nm and green narrowband light having a center wavelength in the vicinity of 540 nm. As an imaging method in the narrowband light observation, there are known a frame sequential method in which the blue narrowband light and the green narrowband light are alternately applied and a monochrome imaging device captures an image whenever each type of light is applied, and a simultaneous method in which the blue narrowband light and the green narrowband light are simultaneously applied and a simultaneous imaging device having color filters captures an image (see U.S. Pat. No. 8,531,512 and US Patent Application Publication No. 2009/0141125). The simultaneous method is inferior in resolution to the frame sequential method, but has the advantages of preventing a blur in the image and structural simplicity of the endoscope system.

The simultaneous imaging device includes a primary color type imaging device having primary color filters and a complementary color type imaging device having complementary color filters. The primary color type imaging device is used in an endoscope system that places importance on color, because of being superior in color reproducibility, though inferior in sensitivity, to the complementary color type imaging device. On the other hand, the complementary color type imaging device, which is superior in sensitivity and inferior in color reproducibility to the primary color type imaging device, is used in an endoscope system that places importance on sensitivity. Since the primary color type imaging device and the complementary color type imaging device have both advantage and disadvantage, it is desired that an endoscope system of the future be available with both of a primary color type endoscope containing the primary color type imaging device and a complementary color type endoscope containing the complementary color type imaging device.

The U.S. Pat. No. 8,531,512 and the US Patent Application Publication No. 2009/0141125 disclose a complementary color type imaging device of a complementary-color checkered-pattern color-difference line sequential method having four types of pixels of magenta (Mg), green (G), cyan (Cy), and yellow (Ye). According to the complementary-color checkered-pattern color-difference line sequential method, pixel signals are read out by a field readout method in a state of mixing (adding) the pixel signals of two adjoining rows. More specifically, the pixel signals are read out in a state of four types of combinations, i.e. the Mg pixel and the Cy pixel, the G pixel and the Ye pixel, the Mg pixel and the Ye pixel, and the G pixel and the Cy pixel. The complementary-color checkered-pattern color-difference line sequential method has the advantage of ease of producing a Y/C signal and an RGB signal just by addition and subtraction of the signals of the four types of mixed pixels.

In the case of performing the narrowband light observation by the endoscope system described above, according to the primary color type imaging device, blue (B) pixels capture the blue narrowband light, and green (G) pixels capture the green narrowband light. Thus, the primary color type imaging device can produce an image that has high color separability and high visibility of the superficial blood vessels (high contrast between the superficial blood vessels and the mucosa membrane). On the contrary, in the complementary color type imaging device, each mixed pixel senses the blue narrowband light and the green narrowband light at the same time (i.e. mixture of colors occurs). This causes low color separability, and a blur of the superficial blood vessels due to the influence of scattered light deteriorates the visibility of the superficial blood vessels.

Also, as described in the US Patent Application Publication No. 2009/0141125 (FIGS. 19 and 21), variations in the spectral sensitivity of pixels vary the amount of a mixed color component, so it is difficult to uniformly perform mixed color correction by an optical method.

Furthermore, even in the primary color type imaging device, in a case where each pixel is sensitive to both of the two types of narrowband light used in the narrowband light observation, the color separability and the visibility of the superficial blood vessels deteriorate, just as in the case of the complementary color type imaging device.

SUMMARY OF THE INVENTION

An object of the present invention is to provide an endoscope system that allows improvement in color separability and visibility of superficial blood vessels in narrowband light observation and an operating method of the endoscope system.

To achieve the above and other objects, an endoscope system according to the present invention includes a light source device, an imaging device, a matrix operation unit, and a mixed color corrector. The light source device simultaneously produces first and second narrowband light having difference wavelength bands. The imaging device has a plurality of types of pixels that sense both of the first and second narrowband light. A signal value is read out of each of the plurality of types of pixels. The matrix operation unit applies a matrix operation to the signal value to produce first and second display signals D1 and D2. The mixed color corrector corrects the first and second display signals D1 and D2 on the basis of the following expression (a):

$$\begin{pmatrix} D1' \\ D2' \end{pmatrix} = \begin{pmatrix} 1 & -K_2 \\ -K_1 & 1 \end{pmatrix} \begin{pmatrix} D1 \\ D2 \end{pmatrix} \quad (a)$$

wherein, $K_1$ is a first correction coefficient representing the ratio of a signal value of the second display signal to a signal value of the first display signal under independent application of only the first narrowband light. $K_2$ is a second correction coefficient representing the ratio of a signal value of the first display signal to a signal value of the second display signal under independent application of only the second narrowband light.

It is preferable that the endoscope system further include a correction coefficient obtaining unit for calculating the first and second correction coefficients $K_1$ and $K_2$, on the basis of the signal values of the first and second display signals obtained under independent application of each of the first and second narrowband light from the light source device.

The imaging device is preferably a complementary color type imaging device. Signal values of a plurality of types of mixed pixels are read out of the imaging device. The matrix operation unit preferably produces the first and second display signals D1 and D2 by performing the matrix operation of the signal values of the plurality of types of mixed pixels.

The complementary color type imaging device preferably has a matrix of at least four types of pixels for performing photoelectric conversion of light of different colors. Two types of the four types of pixels next to in a vertical scan direction preferably compose a first mixed pixel. Other two types of the four types of pixels next to in the vertical scan direction preferably compose a second mixed pixel.

Each of the four types of pixels preferably has one of color filter segments of cyan, magenta, yellow, and green arranged in a checkered pattern. The plurality of types of mixed pixels preferably include the first mixed pixel being a combination of a magenta pixel and a cyan pixel, and the second mixed pixel being a combination of a green pixel and a yellow pixel. The first narrowband light preferably has a center wavelength in a blue or violet wavelength range, and the second narrowband light preferably has a center wavelength in a green wavelength range.

The matrix operation unit preferably performs the matrix operation so as to make a signal of the first mixed pixel as a main signal of the first display signal D1 and make a signal of the second mixed pixel as a main signal of the second display signal D2.

It is preferable that a complementary color type endoscope having the complementary color type imaging device and a primary color type endoscope having a primary color type imaging device be detachably connected to the light source device.

Each of the complementary color type endoscope and the primary color type endoscope preferably has information storage for storing specific information. The endoscope system preferably includes a controller for reading out the specific information from the information storage of the complementary color type endoscope or the primary color type endoscope that is connected to the light source device, in order to judge the type of the connected endoscope.

The information storage preferably stores the first and second correction coefficients $K_1$ and $K_2$. Upon connecting the complementary color type endoscope or the primary color type endoscope to the light source device, the controller preferably reads out the first and second correction coefficients $K_1$ and $K_2$ from the information storage, and enters the first and second correction coefficients $K_1$ and $K_2$ into the mixed color corrector.

An endoscope system according to the present invention includes a light source device, an imaging device, a matrix operation unit, and a mixed color corrector. The light source device simultaneously produces first and second narrowband light having difference wavelength bands. The imaging device has a plurality of types of pixels that sense both of the first and second narrowband light. A signal value is read out of each of the plurality of types of pixels. The matrix operation unit applies a matrix operation to the signal value to produce first and second display signals D1 and D2. The mixed color corrector for correcting the first and second display signals D1 and D2 on the basis of the following expression (b):

$$\begin{pmatrix} D1' \\ D2' \end{pmatrix} = \begin{pmatrix} 1 & R_1 \\ R_2 & 1 \end{pmatrix} \begin{pmatrix} 1 & -K_2 \\ -K_1 & 1 \end{pmatrix} \begin{pmatrix} D1 \\ D2 \end{pmatrix} \quad (b)$$

wherein, $K_1$ is a first correction coefficient representing the ratio of a signal value of the second display signal to a signal value of the first display signal under independent application of only the first narrowband light. $K_2$ is a second correction coefficient representing the ratio of a signal value of the first display signal to a signal value of the second display signal under independent application of only the second narrowband light. $R_1$ is a first color mixture rate representing the rate of a second narrowband light component within a corrected first display signal D1'. $R_2$ is a second color mixture rate representing the rate of a first narrowband light component within a corrected second display signal D2'.

It is preferable that a complementary color type endoscope having a complementary color type imaging device as the imaging device and a primary color type endoscope having a primary color type imaging device as the imaging device be detachably connected to the light source device. Each of the complementary color type endoscope and the primary color type endoscope preferably includes information storage for storing the first and second color mixture rates $R_1$ and $R_2$. The endoscope system preferably includes a controller for reading out the first and second color mixture rates $R_1$ and $R_2$ from the information storage and entering the first and second color mixture rates $R_1$ and $R_2$ into the mixed color corrector, upon connecting the complementary color type endoscope or the primary color type endoscope to the light source device.

It is preferable that the endoscope system further includes a structure enhancement processor for applying blood vessel enhancement processing to an image produced based on the corrected first and second display signals D1' and D2'. The structure enhancement processor preferably increases the degree of enhancement of a superficial blood vessel with increase in the first color mixture rate $R_1$.

An operating method of an endoscope system according to the present invention includes the steps of simultaneously producing first and second narrowband light having difference wavelength bands from a light source device; outputting a signal value from each of a plurality of types of pixels of an imaging device, each of the pixels sensing both of the first and second narrowband light; applying a matrix operation to the signal value and producing first and second display signals D1 and D2 by a matrix operation unit; and correcting the first and second display signals D1 and D2 by a mixed color corrector on the basis of the following expression (c):

$$\begin{pmatrix} D1' \\ D2' \end{pmatrix} = \begin{pmatrix} 1 & -K_2 \\ -K_1 & 1 \end{pmatrix} \begin{pmatrix} D1 \\ D2 \end{pmatrix} \quad (c)$$

wherein, $K_1$ is a first correction coefficient representing the ratio of a signal value of the second display signal to a signal value of the first display signal under independent application of only the first narrowband light. $K_2$ is a second correction coefficient representing the ratio of a signal value of the first display signal to a signal value of the second display signal under independent application of only the second narrowband light.

According to the present invention, the first and second display signals D1 and D2 are produced by the matrix operation of the signal values of the plurality types of pixels, which sense both of the first and second narrowband light. The first and second display signals D1 and D2 are subjected to the mixed color correction. Therefore, in the narrowband light observation, it is possible to improve the color separability and the visibility of the superficial blood vessels.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

First Embodiment

Figure 1:
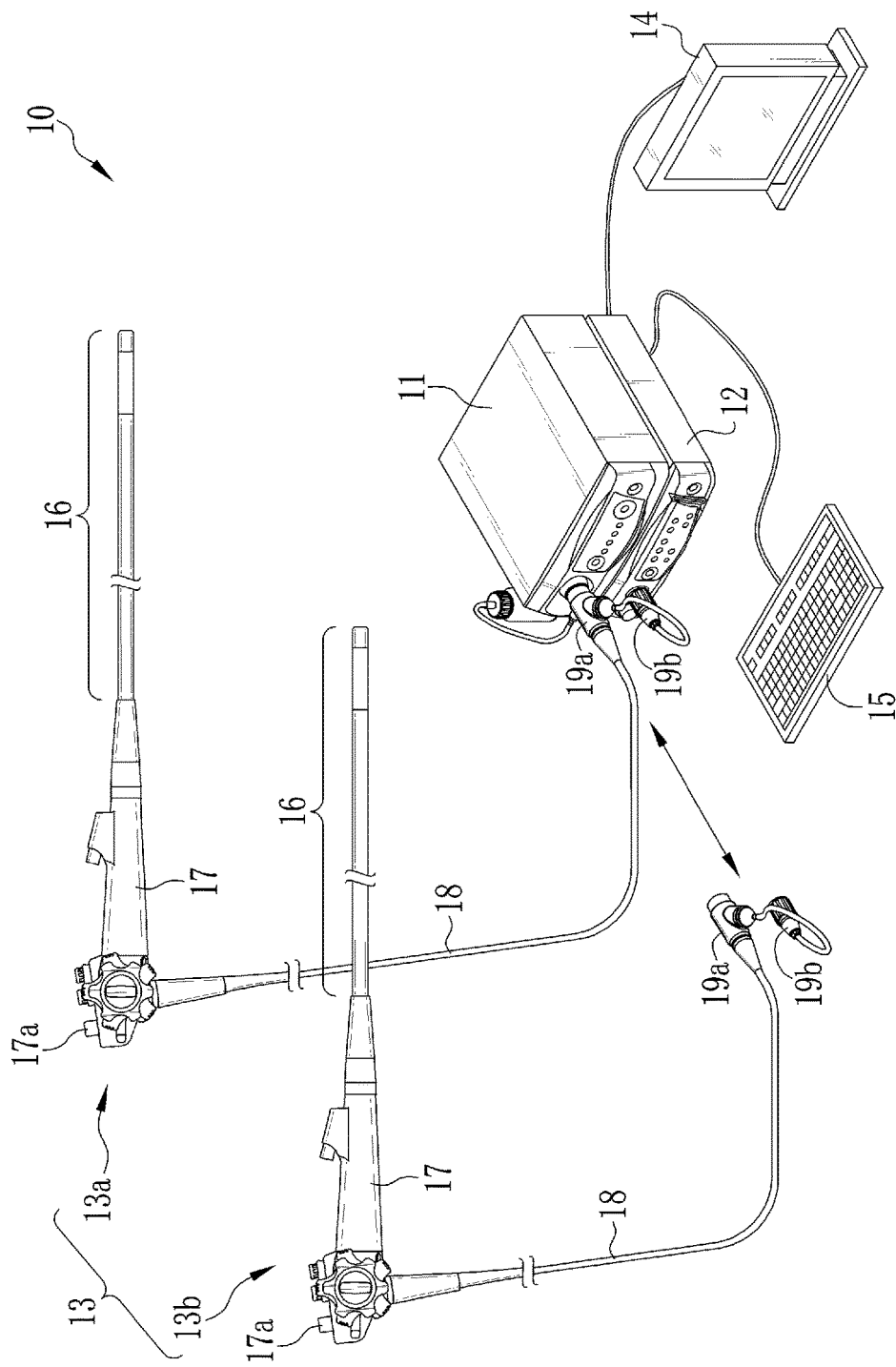
FIG. 1 is a schematic view of an endoscope system.

In FIG. 1, an endoscope system 10 is constituted of a light source device 11, a processor device 12, and electronic endoscopes 13 (hereinafter simply called endoscopes) detachably connected to the light source device 11 and the processor device 12. The light source device 11 produces illumination light and supplies the endoscope 13 with the illumination light. A distal end of the endoscope 13 is inserted into a human body cavity or the like to image the inside of the body cavity. The processor device 12 controls the imaging operation of the endoscope 13, and applies signal processing to an imaging signal obtained by the endoscope 13.

To the processor device 12, an image display device 14 and an input device 15 are connected. The image display device 14, being a liquid crystal display or the like, displays an image of an observation object inside the body cavity produced by the processor device 12. The input device 15, including a keyboard and a mouse, is used for inputting various types of information to the processor device 12.

Figure 2:
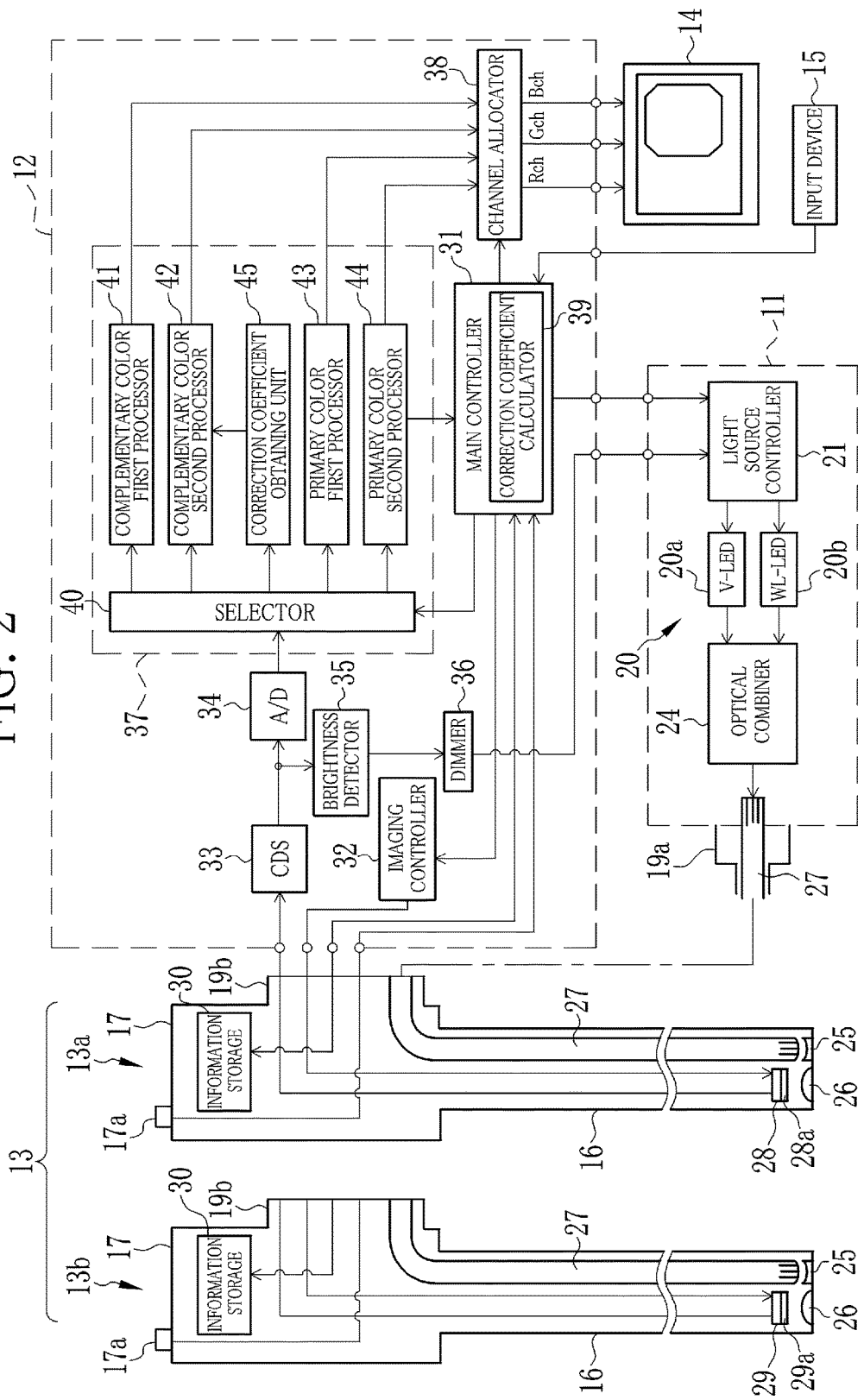
FIG. 2 is a block diagram of the endoscope system.

The endoscopes 13 include a complementary color type endoscope 13a having a complementary color type imaging device 28 (see FIG. 2) and a primary color type endoscope 13b having a primary color type imaging device 29 (see FIG. 2). Either of the complementary color type endoscope 13a and the primary color type endoscope 13b is connectable to the light source device 11 and the processor device 12. The complementary color type endoscope 13a and the primary color type endoscope 13b have identical structure except for the imaging device. Each endoscope 13a or 13b includes an insert section 16, a control handle unit 17, a universal cable 18, a light guide connector 19a, and a signal connector 19b.

The slender insert section 16 is introduced into the human body cavity or the like. The control handle unit 17 is coupled to a rear end of the insert section 16. The control handle unit 17 is provided with various switches, a bending operation dial, and the like. The various switches include a mode switch 17a for switching an operation mode.

The universal cable 18 extends from the control handle unit 17. The light guide connector 19a and the signal connector 19b are attached to an end of the universal cable 18. The light guide connector 19a is detachably connected to the light source device 11. The signal connector 19b is detachably connected to the processor device 12.

As an observation mode of the endoscope system 10, there are provided a normal light observation mode and a narrowband light observation mode. In the normal light observation mode, the observation object is imaged under irradiation with normal light (white light) having a wavelength band extending from the blue region to the red region, and a normal image is produced. In the narrowband light observation mode, the observation object is imaged under irradiation with narrowband light (violet narrowband light Vn and green narrowband light Gn, described later on) having a narrow wavelength band, and a narrowband light image is produced. Both of the complementary color type endoscope 13a and the primary color type endoscope 13b can carry out the normal light observation mode and the narrowband light observation mode.

The endoscope system 10 is switchable between the normal light observation mode and the narrowband light observation mode by operation of the mode switch 17a described above, but may be switched by operation of a foot switch (not shown) connected to the processor device 12, a button provided on a front panel of the processor device 12, the input device 15, or the like.

Figure 3:
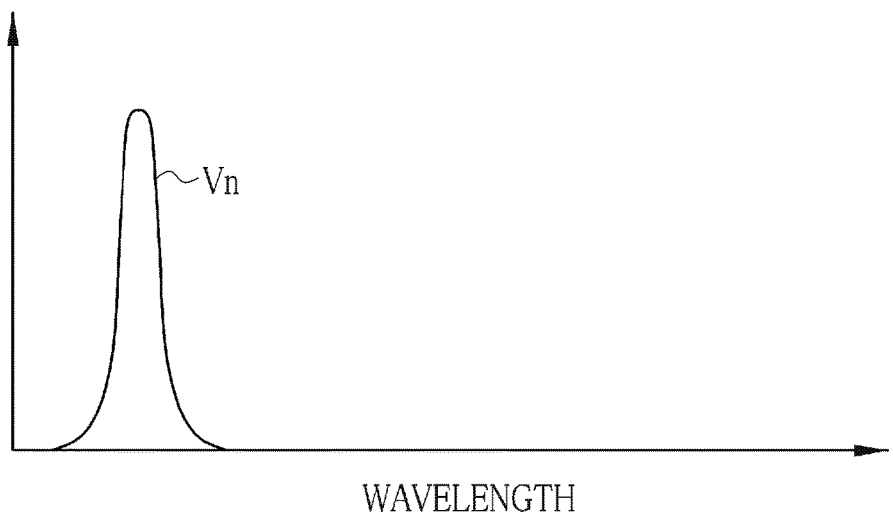
FIG. 3 is a graph showing an emission spectrum of violet narrowband light.
Figure 4:
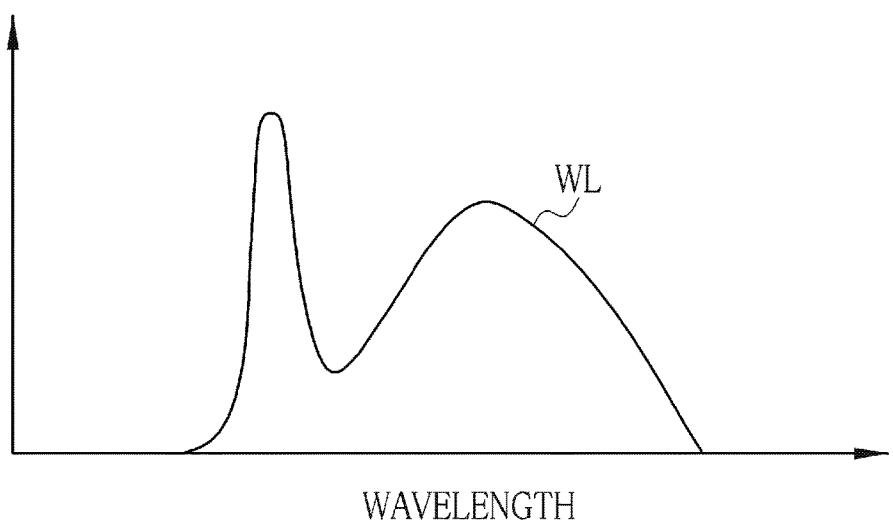
FIG. 4 is a graph showing an emission spectrum of normal light.

In FIG. 2, the light source device 11 has an LED (light emitting diode) light source 20, a light source controller 21, and an optical combiner 24. The LED light source 20 includes a violet LED (V-LED) 20a and a white LED (WL-LED) 20b. The V-LED 20a produces violet narrowband light Vn having a light intensity spectrum as shown in FIG. 3 in which a wavelength band extends from 380 to 440 nm and a center wavelength is at approximately 405 nm. The WL-LED 20b produces white light WL of a wide wavelength band having a light intensity spectrum as shown in FIG. 4. The light source controller 21 controls light emission from the V-LED 20a and the WL-LED 20b.

Figure 5:
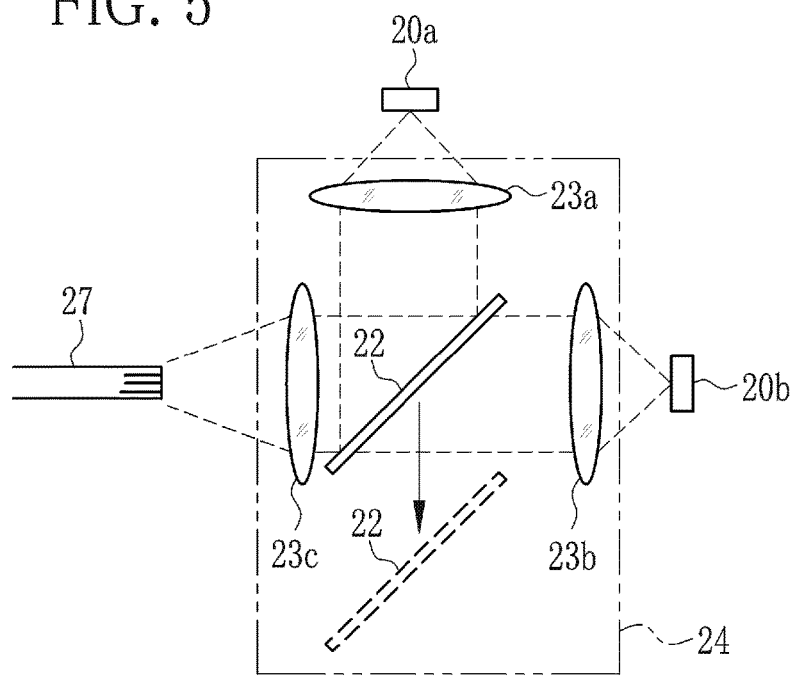
FIG. 5 is an explanatory view of the structure of an optical combiner.

As shown in FIG. 5, the optical combiner 24 has a dichroic mirror 22 and first to third lenses 23a to 23c. The first lens 23a is disposed in front of the LED 20a, and gathers and collimates the light emitted from the LED 20a. The second lens 23b is disposed in front of the LED 20b, and gathers and collimates the light emitted from the LED 20b. The V-LED 20a and the WL-LED 20b are disposed such that optical axes of the V-LED 20a and the WL-LED 20b are orthogonal to each other. The dichroic mirror 22 is situated at an intersection point of the optical axes.

Figure 6:
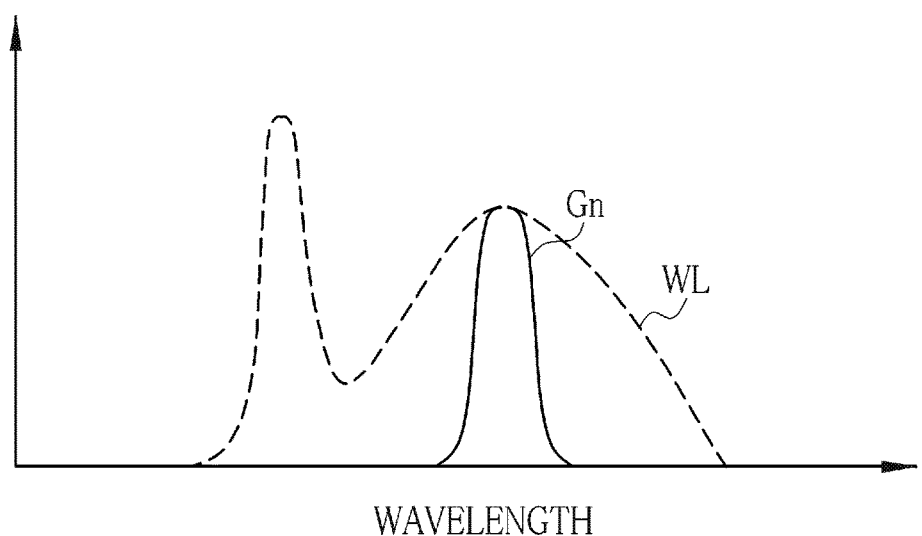
FIG. 6 is a graph showing an emission spectrum of green narrowband light.

The dichroic mirror 22 transmits light in a wavelength band of 530 nm or more and less than 550 nm, and reflects light in a wavelength of less than 530 nm or 550 nm or more, for example. Thus, the violet narrowband light Vn is reflected by the dichroic mirror 22 and gathered by the third lens 23c. On the other hand, a part of the white light WL is passed through the dichroic mirror 22, and gathered by the third lens 23c as green narrowband light Gn having a wavelength band of 530 to 550 nm and a center wavelength of approximately 540 nm, as shown in FIG. 6.

In the narrowband light observation mode, the V-LED 20a and the WL-LED 20b are simultaneously turned on. The violet narrowband light Vn and the green narrowband light Gn are combined (mixed) by the dichroic mirror 22 and gathered by the third lens 23c, and enter a light guide 27.

In the normal light observation mode, a shift mechanism (not shown) moves the dichroic mirror 22 out of the optical axis of the WL-LED 20b. Thus, in the normal light observation mode, the white light WL is directly incident upon the third lens 23c, and led into the light guide 27. Since the dichroic mirror 22 is retracted in the normal light observation mode, the violet narrowband light Vn emitted from the V-LED 20a is not incident upon the third lens 23c even if the dichroic mirror 22 reflects the violet narrowband light Vn.

Thus, the V-LED 20a is preferably turned off in the normal observation mode, but there is no harm in turning on the V-LED 20a.

The center wavelength of the violet narrowband light Vn is approximately 405 nm at which hemoglobin has a high absorption coefficient in the visible region. The center wavelength of the green narrowband light Gn is approximately 540 nm at which hemoglobin has a high absorption coefficient in the green wavelength region. The green narrowband light Gn has a higher reflectance from a mucosa membrane than the violet narrowband light Vn.

The insert section 16 of the endoscope 13 has at its tip end a lighting window and an image capturing window provided next to each other. A lighting lens 25 is fitted into the lighting window. An objective lens 26 is fitted into the image capturing window. The light guide 27 extends through the endoscope 13, and one end of the light guide 27 is opposed to the lighting lens 25. The other end of the light guide 27 is provided with the light guide connector 19a. In a state of fitting the light guide connector 19a to the light source device 11, the other end of the light guide 27 is inserted into the light source device 11.

The lighting lens 25 gathers the light that is transmitted from the light source device 11 through the light guide 27 and ejected from the light guide 27, and applies the light to the observation object inside the body cavity. The objective lens 26 gathers reflected light from living body tissue and the like of the observation object, and forms an optical image. In an image forming position of the objective lens 26, an imaging device (the complementary color type imaging device 28 in the case of the complementary color type endoscope 13a, the primary color type imaging device 29 in the case of the primary color type endoscope 13b) is disposed to capture the optical image and produce the imaging signal. The complementary color type imaging device 28 and the primary color type imaging device 29 are CCD (charge coupled device) image sensors.

Figure 7:
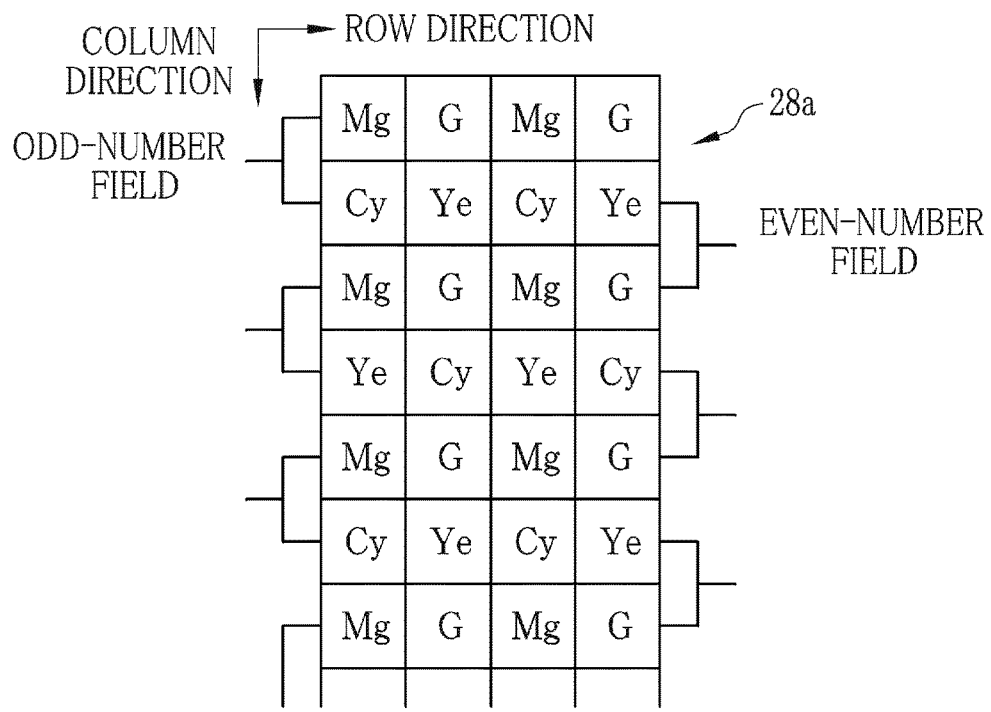
FIG. 7 is a schematic view of a complementary color type color separation filter.

The complementary color type imaging device 28 is provided at its imaging surface with a complementary color type color separation filter 28a to perform optical color separation of the optical image on a pixel-by-pixel basis. As shown in FIG. 7, this complementary color type color separation filter 28a has four types of color filter segments of magenta (Mg), green (G), cyan (Cy), and yellow (Ye), and one color filter segment is provided for each pixel. Accordingly, the complementary color type imaging device 28 has four types of pixels of Mg, G, Cy, and Ye. The Mg pixels and the G pixels are alternately arranged in odd-number rows, and the Cy pixels and the Ye pixels are alternately arranged in even-number rows, such that the Mg pixel, the Cy pixel, the Mg pixel, the Ye pixel, . . . are arranged in this order in odd-number columns, and the G pixel, the Ye pixel, the G pixel, the Cy pixel . . . are arranged in this order in even-number columns. This color filter pattern is referred to as a complementary-color checkered-pattern color-difference line sequential method. A row direction refers to a horizontal scan direction, and a column direction refers to a vertical scan direction.

Figure 8:
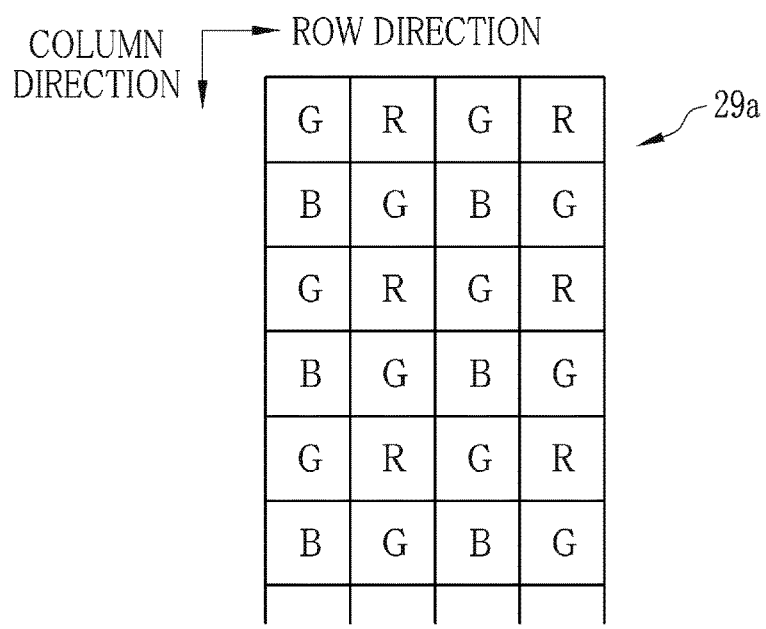
FIG. 8 is a schematic view of a primary color type color separation filter.

The primary color type imaging device 29 is provided at its imaging surface with a primary color type color separation filter 29a. As shown in FIG. 8, this primary color type color separation filter 29a has three types of color filter segments of red (R), green (G), and blue (B), which are three primary colors of an additive color process. One color filter segment is provided for each pixel. Accordingly, the primary color type imaging device 29 has three types of pixels of R, G, and B. The G pixels and the B pixels are alternately arranged in odd-number columns, and the R pixels and the G pixels are alternately arranged in even-number columns. The G pixels and the R pixels are alternately arranged in odd-number rows, and the B pixels and the G pixels are alternately arranged in even-number rows. This color filter pattern is referred to as a primary color Bayer pattern.

The endoscope 13 includes information storage 30 composed of a non-volatile memory such as a flash memory. The information storage 30 stores specific information (the color filter pattern and the pixel number of the imaging device) and the like of the endoscope 13.

The processor device 12 has a main controller 31, an imaging controller 32, a correlated double sampling (CDS) circuit 33, an A/D converter 34, a brightness detector 35, a dimmer 36, a signal processing unit 37, and a channel allocator 38.

The main controller 31 controls each part of the processor device 12 and the light source device 11. Upon connecting the endoscope 13 to the light source device 11 and the processor device 12, the main controller 31 reads the specific information of the endoscope 13 from the information storage 30, and judges whether the connected endoscope 13 is the complementary color type endoscope 13a or the primary color type endoscope 13b. The imaging controller 32 actuates the imaging device (complementary color type imaging device 28 or the primary color type imaging device 29) in accordance with the type of the endoscope 13 judged by the main controller 31.

Figure 9:
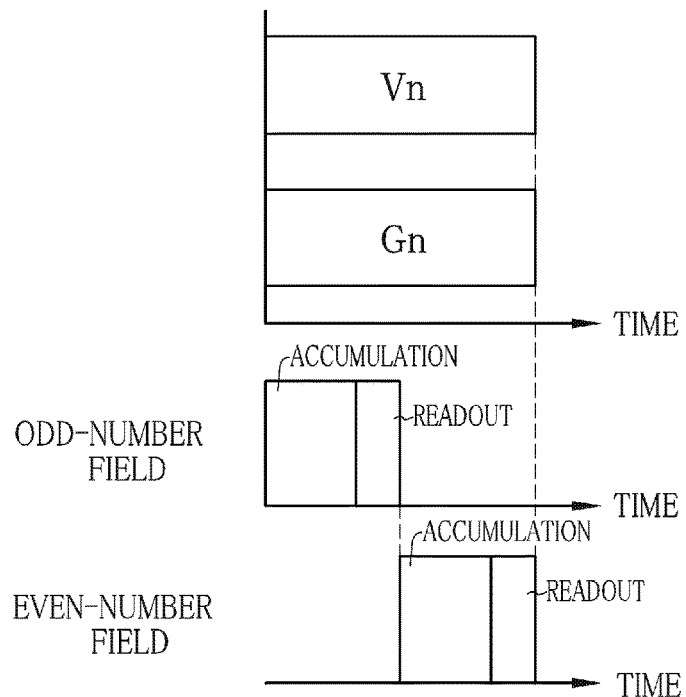
FIG. 9 is a timing chart of light sources and a complementary color type imaging device in a narrowband light observation mode.

In the case of the complementary color type imaging device 28, the imaging controller 32 drives the complementary color type imaging device 28 by a field readout method in synchronization with emission timing of the light source device 11. To be more specific, according to the field readout method, pixel signals of two pixels adjoining in the column direction (vertical scan direction) are read out in a mixed (added) manner in reading each of an odd-number field and an even-number field (see FIG. 7). The mixture of the pixel signals is performed in a horizontal transfer path (not shown) of the CCD image sensor by using the pixel signals of two rows. FIG. 9 shows a timing chart of the narrowband light observation mode. A timing chart of the normal light observation mode is the same as that of the narrowband light observation mode, except that the illumination light is the white light WL.

Figure 10:
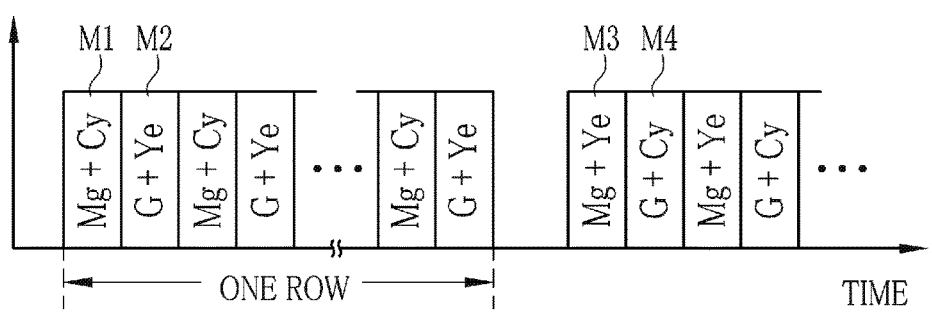
FIG. 10 is an explanatory view of output signals from the complementary color type imaging device.

According to the field readout method, as shown in FIG. 10, a mixed pixel signal (hereinafter called a first mixed pixel signal) M1 of the Mg pixel and the Cy pixel, a mixed pixel signal (hereinafter called a second mixed pixel signal) M2 of the G pixel and the Ye pixel, a mixed pixel signal (hereinafter called a third mixed pixel signal) M3 of the Mg pixel and the Ye pixel, and a mixed pixel signal (hereinafter called a fourth mixed pixel signal) M4 of the G pixel and the Cy pixel are read out from the complementary color type imaging device 28 in each of the odd-number field and the even-number field.

Figure 11:
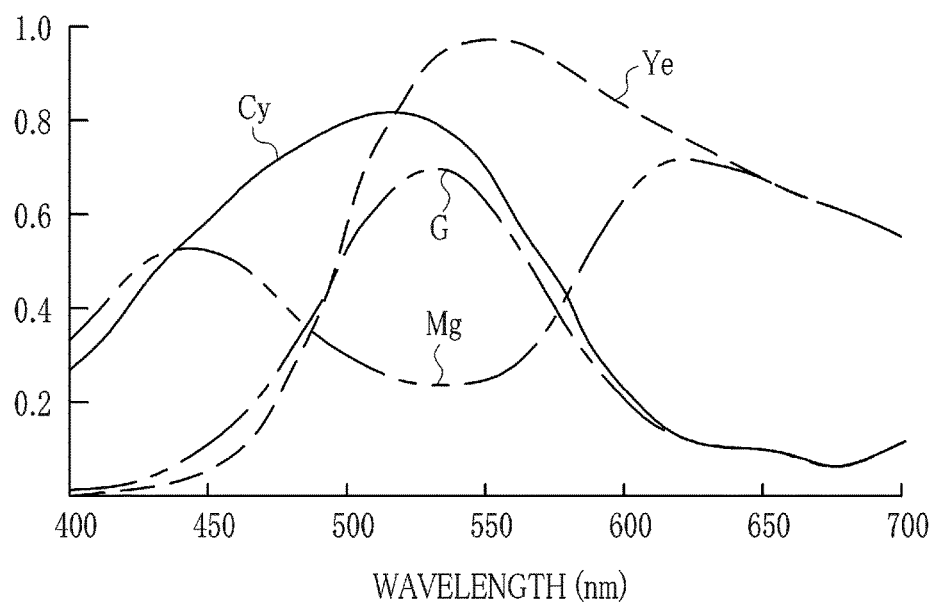
FIG. 11 is a graph of spectral sensitivity characteristics of the complementary color type imaging device.
Figure 12:
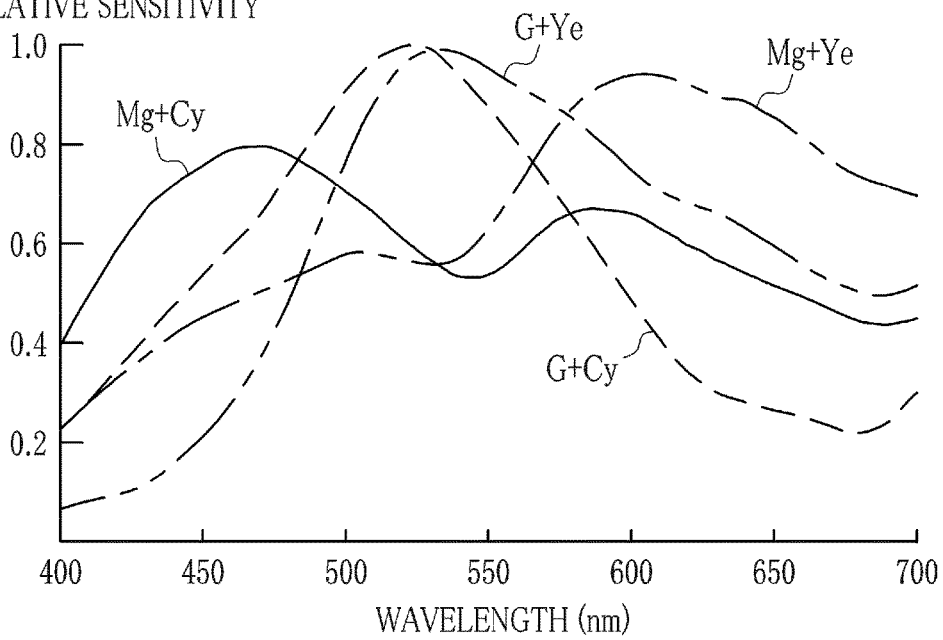
FIG. 12 is a graph of spectral sensitivity characteristics of first to fourth mixed pixels.

Since the pixels of the complementary color type imaging device 28 have spectral sensitivity characteristics as shown in FIG. 11, for example, in accordance with the color filter segments provided thereto, the mixed pixels have spectral sensitivity characteristics as shown in FIG. 12, for example. According to the spectral sensitivity characteristics, out of the first to fourth mixed pixels, the first mixed pixel (Mg+Cy) is the most sensitive to the violet narrowband light Vn (a center wavelength of 405 nm), and the second mixed pixel (G+Ye) is the most sensitive to the green narrowband light Gn (a center wavelength of 540 nm). However, the first mixed pixel (Mg+Cy) has high sensitivity to the green narrowband light Gn too. The second mixed pixel (G+Ye) has a little sensitivity to the violet narrowband light Vn.

In the case of the primary color type imaging device 29, the imaging controller 32 drives the primary color type imaging device 29 by a well-known progressive readout method in synchronization with emission timing of the light source device 11. According to the progressive readout method, the pixel signals of one frame are read out sequentially and individually on a row-by-row basis, without mixing the pixel signals.

A signal outputted from the complementary color type imaging device 28 or the primary color type imaging device 29 is inputted to the CDS circuit 33. The CDS circuit 33 applies correlated double sampling to the inputted signal to remove a noise component occurring in the CCD image sensor. The signal, after the noise removal by the CDS circuit 33, is inputted to the A/D converter 34 and the brightness detector 35. The A/D converter 34 converts the signal inputted from the CDS circuit 33 into a digital signal, and inputs the digital signal to the signal processing unit 37.

The brightness detector 35 detects as brightness (average luminance of the signal) an average value of G signals, in general, based on the signal inputted from the CDS circuit 33. The dimmer 36 produces a dimming signal, which represents the difference between a brightness signal detected by the brightness detector 35 and standard brightness (a target dimming value). This dimming signal is inputted to the light source controller 21. The light source controller 21 adjusts the light emission amount of the LED light source 20 so as to obtain the standard brightness.

Upon receiving a mode switching signal issued by the operation of the mode switch 17a of the endoscope 13, the main controller 31 switches a light emission method of the light source device 11 and a signal processing method of the signal processing unit 37 in accordance with the received mode switching signal.

The signal processing unit 37 includes a selector 40, a complementary color first processor 41, a complementary color second processor 42, a primary color first processor 43, a primary color second processor 44, and a correction coefficient obtaining unit 45. The selector 40 chooses one of the processors 41 to 45 in accordance with the type and the operation mode of the endoscope 13 judged by the main controller 31.

The complementary color first processor 41 is chosen in a case where the endoscope 13 is of the complementary color type and the observation mode is the normal light observation mode. To the complementary color first processor 41, the first to fourth mixed pixel signals M1 to M4 (see FIG. 10) are inputted from the complementary color type imaging device 28. The complementary color first processor 41 produces a luminance signal Y and color difference signals Cr and Cb by performing a well-known Y/C conversion used in the complementary-color checkered-pattern color-difference line sequential method, and then converts the luminance signal Y and the color difference signals Cr and Cb into an RGB signal by a matrix operation. This RGB signal is sent to the channel allocator 38. More specifically, the luminance signal Y and the color difference signals Cr and Cb are calculated by addition and subtraction of the first mixed pixel signal M1 and the second mixed pixel signal M2 next to each other in the row direction and addition and subtraction of the third mixed pixel signal M3 and the fourth mixed pixel signal M4 next to each other in the row direction.

Figure 13:
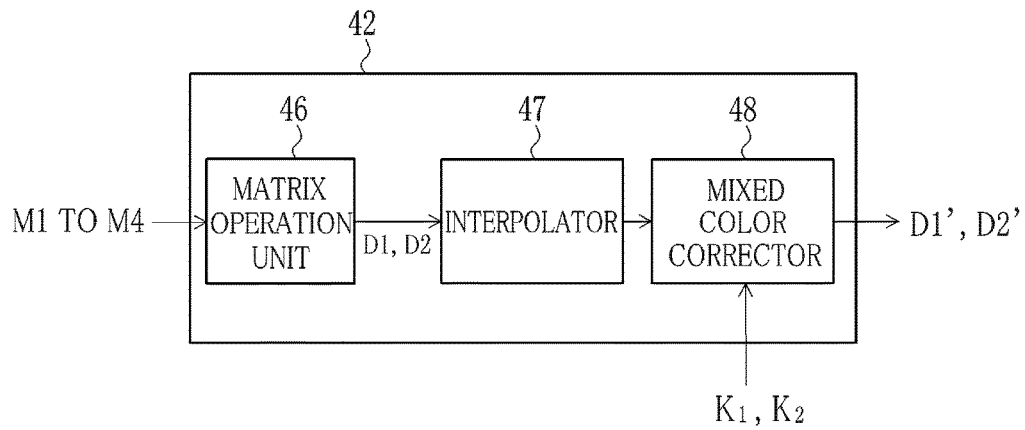
FIG. 13 is a block diagram of a complementary color first processor.

The complementary color second processor 42 is chosen in a case where the endoscope 13 is of the complementary color type and the observation mode is the narrowband light observation mode. As shown in FIG. 13, the complementary color second processor 42 has a matrix operation unit 46, an interpolator 47, and a mixed color corrector 48.

The matrix operation unit 46 applies a matrix operation represented by the following expression (1) to each group of the first to fourth mixed pixel signals M1 to M4 inputted from the complementary color type imaging device 28, and produces first and second display signals D1 and D2. To be more specific, for example, the matrix operation is performed with assigning as one group the first to fourth mixed pixel signals M1 to M4 of relative positional relation as shown in FIG. 10.

$$\begin{pmatrix} D1 \\ D2 \end{pmatrix} \begin{pmatrix} \alpha_{11} & \alpha_{12} & \alpha_{13} & \alpha_{14} \\ \alpha_{21} & \alpha_{22} & \alpha_{23} & \alpha_{24} \end{pmatrix} \begin{pmatrix} M1 \\ M2 \\ M3 \\ M4 \end{pmatrix} \quad (1)$$

Although details will be described later, in the narrowband light observation mode, the violet narrowband light Vn is imaged based on the first display signal D1, and the green narrowband light Gn is imaged based on the second display signal D2. Eight coefficients $\alpha_{11}$ to $\alpha_{24}$ are set at values between or equal to 0 and 1. However, out of the first to fourth mixed pixel signals M1 to M4, the first mixed pixel signal M1 is the most sensitive to the violet narrowband light Vn and the second mixed pixel signal M2 is the most sensitive to the green narrowband light Gn, so the coefficients $\alpha_n$ and $\alpha_{22}$ are set larger than the other coefficients. In other words, the first mixed pixel signal M1 constitutes a main signal of the first display signal D1, and the second mixed pixel signal M2 constitutes a main signal of the second display signal D2. For example, the coefficients $\alpha_{11}$ to $\alpha_{24}$ may be simply set at $\alpha_{11}=\alpha_{22}=1$ and $\alpha_{12}=\alpha\alpha_{13}=\alpha_{14}=\alpha_{21}=a_{23}=\alpha_{24}=0$ (namely, D1=M1 and D2=M2).

The first and second display signals D1 and D2 produced by the matrix operation unit 46 are inputted to the interpolator 47. The interpolator 47 performs a well-known pixel interpolation processing, to produce a pair of the first and second display signals D1 and D2 in each pixel position. The mixed color corrector 48 performs mixed color correction processing by using the following expression (2).

$$\begin{pmatrix} D1' \\ D2' \end{pmatrix} = \begin{pmatrix} 1 & -K_2 \\ -K_1 & 1 \end{pmatrix} \begin{pmatrix} D1 \\ D2 \end{pmatrix} \quad (2)$$

Wherein, $K_1$ represents the ratio (D2v/D1v) of a second display signal D2v to a first display signal D1v obtained under independent application of only the violet narrowband light Vn. $K_2$ represents the ratio (D1g/D2g) of a first display signal D1g to a second display signal D2g obtained under independent application of only the green narrowband light Gn.

Figure 14:
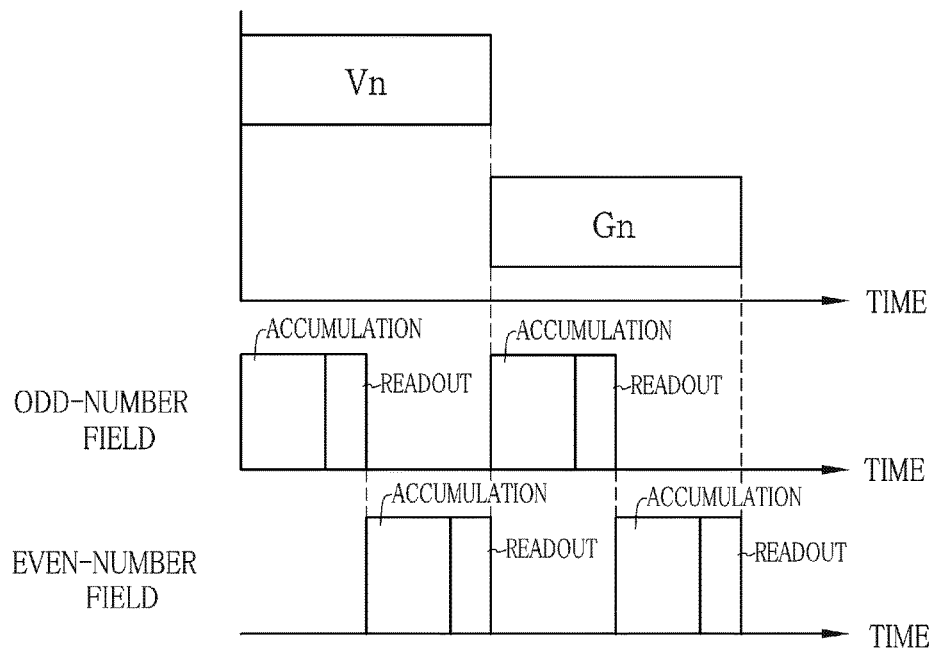
FIG. 14 is a timing chart of the light sources and the complementary color type imaging device in a calibration mode.

The endoscope system 10 has a calibration mode to obtain the correction coefficients $K_1$ and $K_2$. The calibration mode is chosen by operation of the input device 15 or the like. In the calibration mode, the main controller 31 turns on the V-LED 20a and the WL-LED 20b independently, in a state of disposing the dichroic mirror 22 at the intersection point of the optical axes of the V-LED 20a and the WL-LED 20b. Thus, as shown in FIG. 14, the violet narrowband light Vn and the green narrowband light Gn are applied in a time sharing manner, and the complementary color type imaging device 28 is driven in synchronization with emission timing.

In the calibration mode, the correction coefficient obtaining unit 45 calculates the above first display signals D1v and D1g and the above second display signals D2g and D2v by the matrix operation based on the expression (1), and calculates the correction coefficients $K_1$ and $K_2$ with the use of the relational expressions $K_1=D2v/D1v$ and $K_2=D1g/D2g$. The correction coefficients $K_1$ and $K_2$ are preferably calculated by using each average of a plurality of first display signals D1v and D1g and a plurality of second display signals D2g and D2v. The correction coefficients $K_1$ and $K_2$ obtained by the correction coefficient obtaining unit 45 are inputted to the mixed color corrector 48. The mixed color corrector 48 keeps holding the calculated correction coefficients $K_1$ and $K_2$ for use in the mixed color correction processing, until the calibration is performed again.

The correction coefficients $K_1$ and $K_2$ are obtained in the course of manufacture and stored in advance to the information storage 30 of the complementary color type endoscope 13a. Upon connecting the complementary color type endoscope 13a to the light source device 11 and the processor device 12, the main controller 31 reads the correction coefficients $K_1$ and $K_2$ from the information storage 30 and inputs the correction coefficients $K_1$ and $K_2$ to the mixed color corrector 48. If the calibration is performed, the correction coefficients $K_1$ and $K_2$ stored in the information storage 30 of the complementary color type endoscope 13a are deleted and replaced with the correction coefficients $K_1$ and $K_2$ newly calculated by the mixed color corrector 48.

The mixed color correction processing according to the expression (2) lowers a mixed color component (a green narrowband light Gn component within the first display signal D1 and a violet narrowband light Vn component within the second display signal D2). The first and second display signals D1' and D2' after the mixed color correction are sent to the channel allocator 38.

The primary color first processor 43 is chosen in a case where the endoscope 13 is of the primary color type and the observation mode is the normal light observation mode. To the primary color first processor 43, the RGB signal is inputted from the primary color type imaging device 29. In this RGB signal, one of R, G, and B signals is assigned to each pixel. The primary color first processor 43 produces three signals of R, G, and B for each pixel by performing well-known pixel interpolation processing. The RGB signals produced by the pixel interpolation processing are sent to the channel allocator 38.

The primary color second processor 44 is chosen in a case where the endoscope 13 is of the primary color type and the observation mode is the narrowband light observation mode. To the primary color second processor 44, the RGB signal is inputted from the primary color type imaging device 29. The primary color second processor 44 extracts a B signal for sensing the violet narrowband light Vn and a G signal for sensing the green narrowband light Gn, and produces a B signal and a G signal of each pixel by applying the pixel interpolation processing as with above. The B signal and the G signal are sent to the channel allocator 38.

In the normal light observation mode, the channel allocator 38 receives the RGB signals irrespective of the type of the endoscope 13, and hence allocates the R, G, and B signals to an R channel, a G channel, and a B channel of the image display device 14, respectively. Therefore, the normal image, that is, an image of the observation object irradiated with the normal light is displayed on the image display device 14.

In a case where the endoscope 13 is of the complementary color type and the narrowband light observation mode is chosen, the channel allocator 38 assigns the first and second display signals D1' and D2' inputted from the complementary color second processor 42 to the channels of the image display device 14 as indicated by the following expression (3):

$$\begin{pmatrix} Rch \\ Gch \\ Bch \end{pmatrix} = \begin{pmatrix} 0 & 1 \\ 1 & 0 \\ 1 & 0 \end{pmatrix} \begin{pmatrix} D1' \\ D2' \end{pmatrix} \quad (3)$$

Therefore, an image of the observation object irradiated with the violet narrowband light Vn and the green narrowband light Gn is displayed as the special image on the image display device 14. Since the expression (3) assigns the first display signal D1', which is highly sensitive to the violet narrowband light Vn, to the two channels, the special image is such an image in which the structure of superficial blood vessels (blood capillary) and the like in the vicinity of the surface of a living body is easily visible. Note that, the first and second display signals D1' and D2' may be weighted by coefficients other than "0" or "1" in assignment to the channels.

Furthermore, provided that the endoscope 13 is of the primary color type and the narrowband light observation mode is chosen, the channel allocator 38 assigns the B signal and the G signal inputted from the primary color second processor 44 to the channels of the image display device 14 as indicated by the following expression (4):

$$\begin{pmatrix} Rch \\ Gch \\ Bch \end{pmatrix} = \begin{pmatrix} 0 & 1 \\ 1 & 0 \\ 1 & 0 \end{pmatrix} \begin{pmatrix} B \\ G \end{pmatrix} \quad (4)$$

Thus, an image of the observation object irradiated with the violet narrowband light Vn and the green narrowband light Gn is displayed as the special image on the image display device 14. This special image is such an image in which the structure of the superficial blood vessels and the like in the vicinity of the surface of the living body is easily visible. In a like manner, the B signal and the G signal may be weighted by coefficients other than "0" or "1" in assignment to the channels.

Next, the operation of the mixed color correction processing will be described. The first and second display signals D1 and D2 are represented by the following expression (5). In this expression, "X" and "Y" represent the light amounts of the violet narrowband light Vn and the green narrowband light Gn, respectively, simultaneously applied from the complementary color endoscope 13*a* to the observation object. "$a_1$" represents average sensitivity of the first display signal D1 to the violet narrowband light Vn. "$b_1$" represents average sensitivity of the first display signal D1 to the green narrowband light Gn. "$a_2$" represents average sensitivity of the second display signal D2 to the green narrowband light Gn. "$b_2$" represents average sensitivity of the second display signal D2 to the violet narrowband light Vn. The average sensitivity refers to an average of sensitivity in the wavelength band of each type of narrowband light.

$$\begin{pmatrix} D1 \\ D2 \end{pmatrix} = \begin{pmatrix} a_1 & b_1 \\ b_2 & a_2 \end{pmatrix} \begin{pmatrix} X \\ Y \end{pmatrix} \quad (5)$$

Using the sensitivity $a_1$, $b_1$, $a_2$, and $b_2$, the correction coefficients $K_1$ and $K_2$ used in the above mixed color correction processing are represented by the following expressions (6) and (7).

$$K_1 = \frac{D2v}{D1v} = \frac{b_2}{a_1} \quad (6)$$

$$K_2 = \frac{D1g}{D2g} = \frac{b_1}{a_2} \quad (7)$$

By applying the mixed color correction processing represented by the expression (2) to the first and second display signals D1 and D2 represented by the expression (5), first and second display signals D1' and D2' after the mixed color correction are represented by the following expressions (8) and (9), and the mixed color components are eliminated.

$$D1' = \left(a_1 - \frac{b_1 b_2}{a_2}\right) X = (1 - K_1 K_2) a_1 X \quad (8)$$

$$D2' = \left(a_2 - \frac{b_1 b_2}{a_1}\right) Y = (1 - K_1 K_2) a_2 Y \quad (9)$$

In the expressions (8) and (9), "$a_1 X$" corresponds to the first display signal D1*v* under independent application of only the violet narrowband light Vn of the light amount X, and "$a_2 Y$" corresponds to the second display signal D2*g* under independent application of only the green narrowband light Gn of the light amount Y. Thus, it is apparent from the expressions (8) and (9) that the signal values of the first and second display signals D1' and D2' after the mixed color correction are lower than those of the first and second display signals D1*v* and D2*g* by the time-sharing application by a multiple of $(1-K_1 K_2)$.

Especially, in the case of $\alpha_{11}=\alpha_{22}=1$ and $\alpha_{12}=\alpha_{13}=\alpha_{14}=\alpha_{21}=\alpha_{23} \leq \alpha_{24}=0$ (namely, D1=M1 and D2=M2), as shown in FIG. 12, $a_1 \approx 0.45$, $a_2 \approx 0$, $b_1 \approx 0.53$, and $b_2 \approx 0.07$. Thus, $(1-K_1 K_2) \approx 0.92$, and hence the rate of decrease of the signal value is of the order of 8%.

Figure 15:
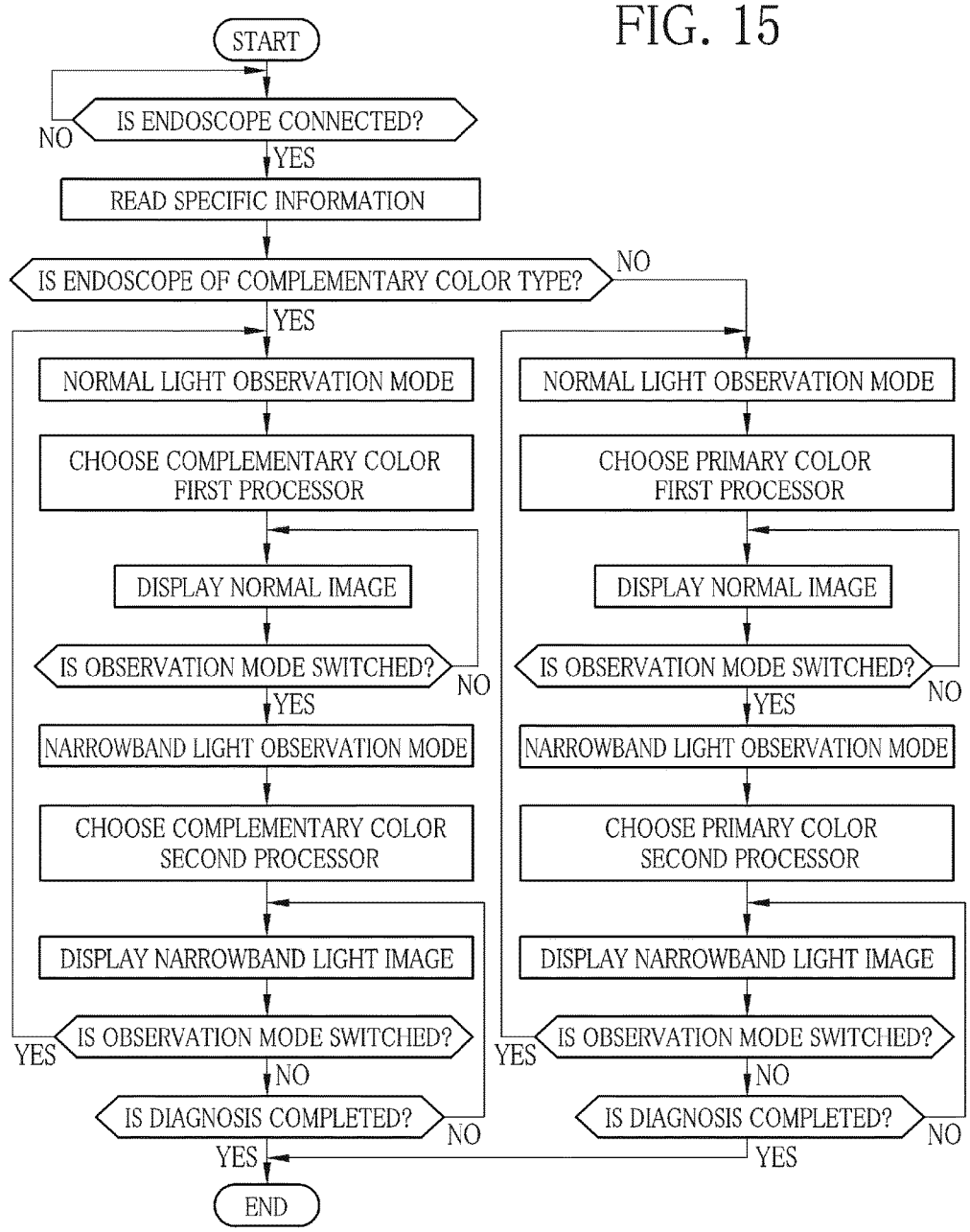
FIG. 15 is a flowchart of the operation of the endoscope system.

Next, the operation of the endoscope system 10 will be described with referring to a flowchart of FIG. 15. Upon connecting the endoscope 13 to the light source device 11 and the processor device 12, the main controller 31 of the processor device 12 reads the specific information from the information storage 30 of the endoscope 13 to judge whether the connected endoscope is the complementary color type endoscope 13*a* or the primary color type endoscope 13*b*. For example, in the case of the complementary color type endoscope 13*a*, the main controller 31 puts the light source device 11 and the processor device 12 into the normal light observation mode, and makes the selector 40 select the complementary color first processor 41 in the signal processing unit 37.

In the normal light observation mode, the dichroic mirror 22 is retracted to a position illustrated by a dotted line in FIG. 5 in the optical combiner 24 of the light source device 11, and the WL-LED 20*b* is turned on. The normal light (white light) WL produced by the WL-LED 20*b* is supplied to the light guide 27 of the complementary color type endoscope 13*a*. Also, the complementary color type imaging device 28 of the complementary color type endoscope 13*a* is driven by the imaging controller 32 by the field readout method, and outputs the first to fourth mixed pixel signals M1 to M4. The first to fourth mixed pixel signals M1 to M4 are subjected to the Y/C processing and converted into the RGB signal in the complementary color first processor 41, and displayed on the image display device 14 through the channel allocator 38. Thus, the normal image captured under the normal light is displayed on the image display device 14.

The insert section 16 of the complementary color type endoscope 13*a* is introduced into a patient's body cavity to perform endoscopy. To inspect the pattern of the superficial blood vessels and the like in tissue to be inspected such as a lesion inside the body cavity, the mode switch 17*a* is operated. The main controller 31 detects the operation signal of the mode switch 17*a*, and the light source device 11 and the processor device 12 are put into the narrowband light observation mode.

In the narrowband light observation mode, the selector 40 selects the complementary color second processor 42. In the narrowband light observation mode, the dichroic mirror 22 is disposed at the intersection point of the optical axes of the V-LED 20*a* and the WL-LED 20*b* in the optical combiner 24, and the V-LED 20*a* and the WL-LED 20*b* are turned on simultaneously. The narrowband light, being the mixture of the violet narrowband light Vn and the green narrowband light Gn, is produced by the optical combiner 24, and supplied to the light guide 27 of the complementary color type endoscope 13*a*. The complementary color type imaging device 28 is driven by the field readout method, and outputs the first to fourth mixed pixel signals M1 to M4.

In the complementary color second processor 42, the matrix operation unit 46 performs the matrix operation of the first to fourth mixed pixel signals M1 to M4, and produces the first and second display signals D1 and D2. Then, the interpolator 47 applies the pixel interpolation processing to the first and second display signals D1 and D2, and then the mixed color corrector 48 applies the above mixed color correction processing to the first and second display signals D1 and D2. After the mixed color correction, the channel allocator 38 assigns the second display signal D2' to the R channel and assigns the first display signal D1' to the G channel and the B channel, so that the first and second display signals D1' and D2' are displayed on the image display device 14. Therefore, the special image captured under the narrowband light is displayed on the image display device 14.

Since the violet narrowband light Vn is transmittable from the surface of the observation object to a first transmission distance in the vicinity of a superficial layer, a first image, which is based on the violet narrowband light Vn, contains much of an image of structure at the first transmission distance, such as the superficial blood vessels. This first image is produced based on the first display signal D1. On the other hand, since the green narrowband light Gn is transmittable from the surface of the observation object to a second transmission distance in the vicinity of a middle to deep layer, a second image, which is based on the green narrowband light Gn, contains much of an image of structure at the second transmission distance, such as middle to deep blood vessels. The second image has high visibility of a minute pattern and the like of the mucosa membrane. This second image is produced based on the second display signal D2. The first image and the second image are combined into the special image.

According to this embodiment, it is possible to eliminate the mixed color components by the mixed color correction processing, and obtain the special image that has improved color separability and improved visibility of the superficial blood vessels (improved contrast between the superficial blood vessels and the mucosa membrane).

The special image is repeatedly displayed until the mode switch 17*a* is operated or completion operation for completing the endoscopy is performed from the input device 15. Upon operating the mode switch 17*a*, the endoscope system 10 is put back into the normal observation mode. The completion operation ends the operation.

On the other hand, in a case where the main controller 31 judges that the primary color type endoscope 13*b* is connected to the light source device 11 and the processor device 12, the light source device 11 and the processor device 12 are put into the normal light observation mode, and the selector 40 selects the primary color first processor 43. In the normal light observation mode, as in the case of the complementary color type, the normal light (white light) WL is produced by the light source device 11 and supplied to the light guide 27 of the primary color type endoscope 13*b*.

In this case, the primary color type imaging device 29 is driven by the progressive readout method and outputs the RGB signal. This RGB signal is subjected to the pixel interpolation processing and the like in the primary color first processor 43, and displayed on the image display device 14 through the channel allocator 38. Thus, the normal image captured under the normal light is displayed on the image display device 14.

After that, upon operating the mode switch 17*a*, the light source device 11 and the processor device 12 are put into the narrowband light observation mode. In the narrowband light observation mode, the selector 40 selects the primary color second processor 44, and the narrowband light, being the mixture of the violet narrowband light Vn and the green narrowband light Gn, is produced by the light source device 11 and supplied to the light guide 27 of the primary color type endoscope 13*b*, just as with the complementary color type.

The primary color type imaging device 29 is driven by the progressive readout method and outputs the RGB signal. Out of the RGB signal, the primary color second processor 44 extracts only the B signal and the G signal. The B signal and the G signal are subjected to the pixel interpolation processing and the like, and displayed on the image display device 14 through the channel allocator 38. Thus, the special image captured under the narrowband light is displayed on the image display device 14.

As in the case of the complementary color type, the special image is displayed repeatedly until the mode switch 17*a* is operated or the completion operation is performed from the input device 15. Upon operating the mode switch 17*a*, the endoscope system 10 is put back into the normal observation mode. The completion operation ends the operation.

In a case where the complementary color type endoscope 13*a* is connected to the light source device 11 and the processor device 12, the calibration for obtaining the correction coefficients $K_1$ and $K_2$ for use in the mixed color correction can be performed by operation of the input device 15 or the like. In the calibration, a white plate or the like is used as an object to be imaged.

In the calibration, the selector 40 selects the correction coefficient obtaining unit 45, and the violet narrowband light Vn and the green narrowband light Gn are applied in a time sharing manner. At this time, the first display signals D1v and D1g and the second display signals D2g and D2v are produced based on the first to fourth mixed pixel signals M1 to M4 outputted from the complementary color type imaging device 28, and the average of each signal value is calculated. Then, the correction coefficients $K_1$ and $K_2$ are calculated from the relational expressions $K_1=D2v/D1v$ and $K_2=D1g/D2g$. The calculated correction coefficients $K_1$ and $K_2$ are inputted to the mixed color corrector 48, and the correction coefficients $K_1$ and $K_2$ that have been stored in the information storage 30 of the complementary color type endoscope 13a are deleted and replaced with the calculated correction coefficients $K_1$ and $K_2$. The correction coefficients $K_1$ and $K_2$ that are stored to the information storage 30 of the complementary color type endoscope 13a are read by the main controller 31 and inputted to the mixed color corrector 48, in the next use of the complementary color type endoscope 13a.

Second Embodiment

Next, an endoscope system according to a second embodiment will be described. The endoscope system according to this embodiment is different from the endoscope system 10 of the first embodiment in terms that the mixed color corrector 48 performs the mixed color correction processing with the use of the following expression (10):

$$\begin{pmatrix} D1' \\ D2' \end{pmatrix} = \begin{pmatrix} 1 & R_1 \\ R_2 & 1 \end{pmatrix} \begin{pmatrix} 1 & -K_2 \\ -K_1 & 1 \end{pmatrix} \begin{pmatrix} D1 \\ D2 \end{pmatrix} \qquad (10)$$

Wherein, $R_1$ is a first color mixture rate that represents the rate of the green narrowband light Gn component within the first display signal D1'. $R_2$ is a second color mixture rate that represents the rate of the violet narrowband light Vn component within the second display signal D2'. $R_1$ and $R_2$ take values between or equal to 0 and 1.

Figure 16:
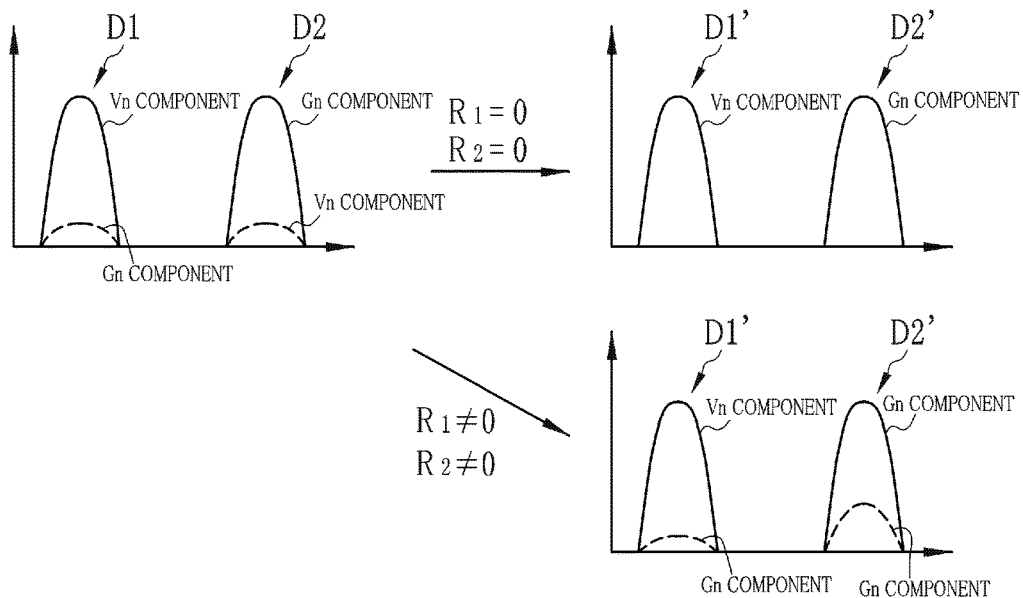
FIG. 16 is an explanatory view of mixed color correction processing of first and second mixed pixel signals in accordance with first and second color mixture rates.

In the case of $R_1=0$ and $R_2=0$, the expression (10) becomes equal to the expression (2), and the mixed color components are completely eliminated, as shown in FIG. 16. On the other hand, in the case of $R_1 \neq 0$ and $R_2 \neq 0$, the green narrowband light Gn component is present within the first display signal D1' in accordance with the first color mixture rate $R_1$, and the violet narrowband light Vn component is present within the second display signal D2' in accordance with the second color mixture rate $R_2$. The first and second display signals D1' and D2' in the case of $R_1 \neq 0$ and $R_2 \neq 0$ are represented by the following expressions (11) and (12):

$$D1'=(1-K_1K_2)(a_1X+R_1a_2Y) \qquad (11)$$

$$D2'=(1-K_1K_2)(a_2Y+R_2a_1X) \qquad (12)$$

Each of the first and second color mixture rates $R_1$ and $R_2$ is set in the mixed color corrector 48 so as to maintain compatibility with an existing light source device (for example, a light source device having a xenon lamp and a narrowband filter for limiting a wavelength). The first and second color mixture rates $R_1$ and $R_2$ may be set in the information storage 30 of the complementary color type endoscope 13a. Upon connecting the complementary color type endoscope 13a to the light source device 11 and the processor device 12, the main controller 31 may obtain the first and second color mixture rates $R_1$ and $R_2$ from the information storage 30 and enter the first and second color mixture rates $R_1$ and $R_2$ into the mixed color corrector 48.

Also, in the case of $R_1=0$ and $R_2=0$, the first and second display signals D1' and D2' have lower signal values than in the case of time-sharing application. If this gap (decrease amount) in signal values is large, the first and second color mixture rates $R_1$ and $R_2$ are preferably determined based on the expressions (11) and (12) such that the first and second display signals D1' and D2' are in a predetermined level.

Figure 17:
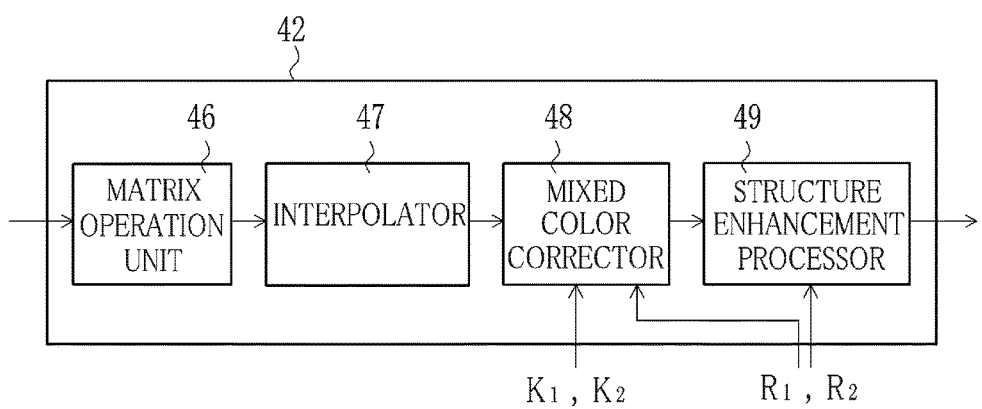
FIG. 17 is a block diagram of the complementary color first processor having a structure enhancement processor.

Also, as shown in FIG. 17, a structure enhancement processor 49 may be provided downstream of the mixed color corrector 48 of the second embodiment. The structure enhancement processor 49 applies structure enhancement processing to the first and second display signals D1' and D2' outputted from the mixed color corrector 48 based on at least one of the first and second color mixture rates $R_1$ and $R_2$. For example, a blood vessel enhancing unit for carrying out frequency filtering, as disclosed in US Patent Application Publication No. 2014/0100427 (corresponding to Japanese Patent Laid-Open Publication No. 2013-013656), may be applied as the structure enhancement processor 49. The higher the first color mixture rate $R_1$, the higher degree of enhancement of the superficial blood vessels is set. This is because the contrast of the superficial blood vessels decreases with increase in the first color mixture rate $R_1$.

Note that, in each of the above embodiments, the mixed color corrector 48 performs the mixed color correction of all the first and second display signals D1 and D2 with the use of a pair of correction coefficients $K_1$ and $K_2$, but the correction coefficients $K_1$ and $K_2$ to be used in the mixed color correction may vary from one pair of the first and second display signals D1 and D2 to another. In this case, for example, the first and second display signals D1 and D2 that are produced from the first to fourth mixed pixel signals M1 to M4 in relative positional relation as shown in FIG. 10 are paired with each other. The correction coefficients $K_1$ and $K_2$ may be calculated on a pair-by-pair basis in the calibration mode with the use of the first and second display signals D1 and D2 obtained under independent application of the violet narrowband light Vn and the green narrowband light Gn.

Also, in each of the above embodiments, the primary color second processor 44 assigns the B signal and the G signal, included in the RGB signal, to the B channel and the G channel, respectively. However, considering a case where each of the RGB signals senses both of the violet narrowband light Vn and the green narrowband light Gn, the primary color second processor 44 may preferably perform the matrix operation and the mixed color correction, as with the complementary color second processor 42.

To be more specific, the RGB signals (pixel signals R, G, and B) inputted to the primary color second processor 44 may be subjected to the matrix operation represented by the following expression (13), to produce the first and second display signals D1 and D2.

$$\begin{pmatrix} D1 \\ D2 \end{pmatrix} \begin{pmatrix} \beta_{11} & \beta_{12} & \beta_{13} \\ \beta_{21} & \beta_{22} & \beta_{23} \end{pmatrix} \begin{pmatrix} B \\ G \\ R \end{pmatrix} \qquad (13)$$

Six coefficients $\beta_{11}$ to $\beta_{23}$ take values between or equal to 0 and 1. More specifically, the coefficients $\beta_{11}$ and $\beta_{22}$ are set larger than the other coefficients. For example, the coefficients $\beta_{11}$ to $\beta_{23}$ may be simply set at $\beta_{11}=\beta_{22}=1$ and $\beta_{12}=\beta_{13}=\beta_{21}=\beta_{23}=0$ (namely, D1=B and D2=G).

The mixed color correction processing is performed based on the expression (2) or (10), just as in the case of the complementary color second processor 42. To obtain the correction coefficients $K_1$ and $K_2$, the violet narrowband light Vn and the green narrowband light Gn are applied in a time sharing manner, and the RGB signal outputted from the primary color imaging device 29 is converted into the first display signals D1$v$ and D1$g$ and the second display signals D2$g$ and D2$v$ by the matrix operation. Then, the correction coefficients $K_1$ and $K_2$ are calculated based on the relational expressions $K_1$=D2$v$/D1$v$ and $K_2$=D1$g$/D2$g$. The correction coefficients $K_1$ and $K_2$ are stored to the information storage 30 of the primary color type endoscope 13$b$, as in the case of the complementary color type. The other operation of the primary color type endoscope 13$b$, including readout of the correction coefficients $K_1$ and $K_2$ from the information storage 30, replacement of the correction coefficients $K_1$ and $K_2$, and the like, is the same as that of the complementary color type, so the description thereof will be omitted.

Figure 18:
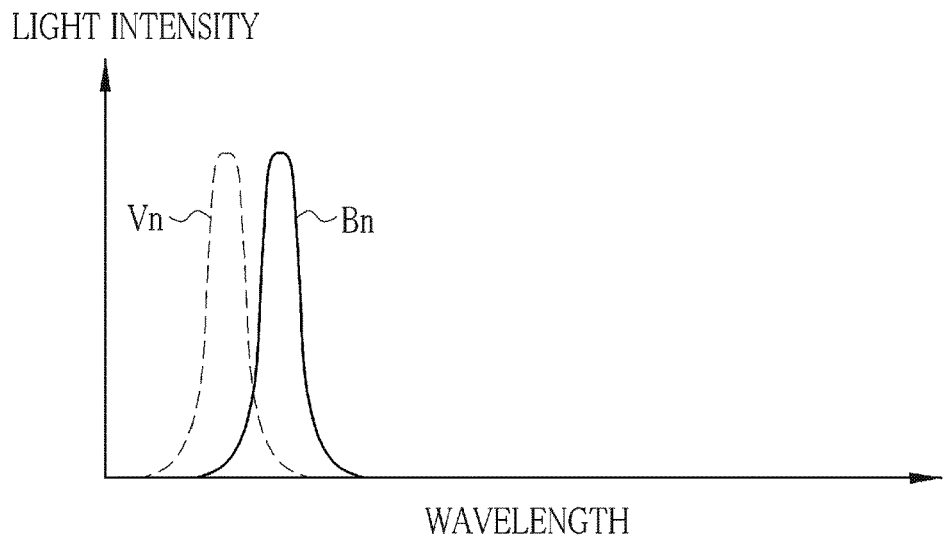
FIG. 18 is a graph showing an emission spectrum of blue narrowband light.

The LED light source 20 contains the V-LED 20$a$ and the WL-LED 20$b$ in the above embodiment, but a blue LED, which emits blue narrowband light Bn having a wavelength band on a longer wavelength side than the violet narrowband light Vn, as shown in FIG. 18, may be used instead of the V-LED 20$a$. The center wavelength of the blue narrowband light Bn is within the confines of approximately 410 nm to 420 nm, and preferably at approximately 415 nm.

Instead of the V-LED 20$a$ and the WL-LED 20$b$, a plurality of LEDs (for example, four LEDs) having different emission wavelength bands may be provided. Turning on all the LEDs produces the normal light (white light), while turning on two of the LEDs produces two types of narrowband light. Furthermore, another type of semiconductor light source such as an LD (laser diode) may be used instead of the LED.

Another light source device that has a lamp for emitting light having a wide wavelength band such as white light and a narrowband filter, as disclosed in U.S. Pat. No. 8,531,512 (corresponding to Japanese Patent No. 4009626) and the like, may be used instead of the light source device 11 described in the above embodiment. This narrowband filter is a two-peak filter, which has band-pass characteristics at two narrow wavelength bands. The narrowband filter is inserted into or retracted from the optical axis of the lamp according to the operation mode.

Figure 19:
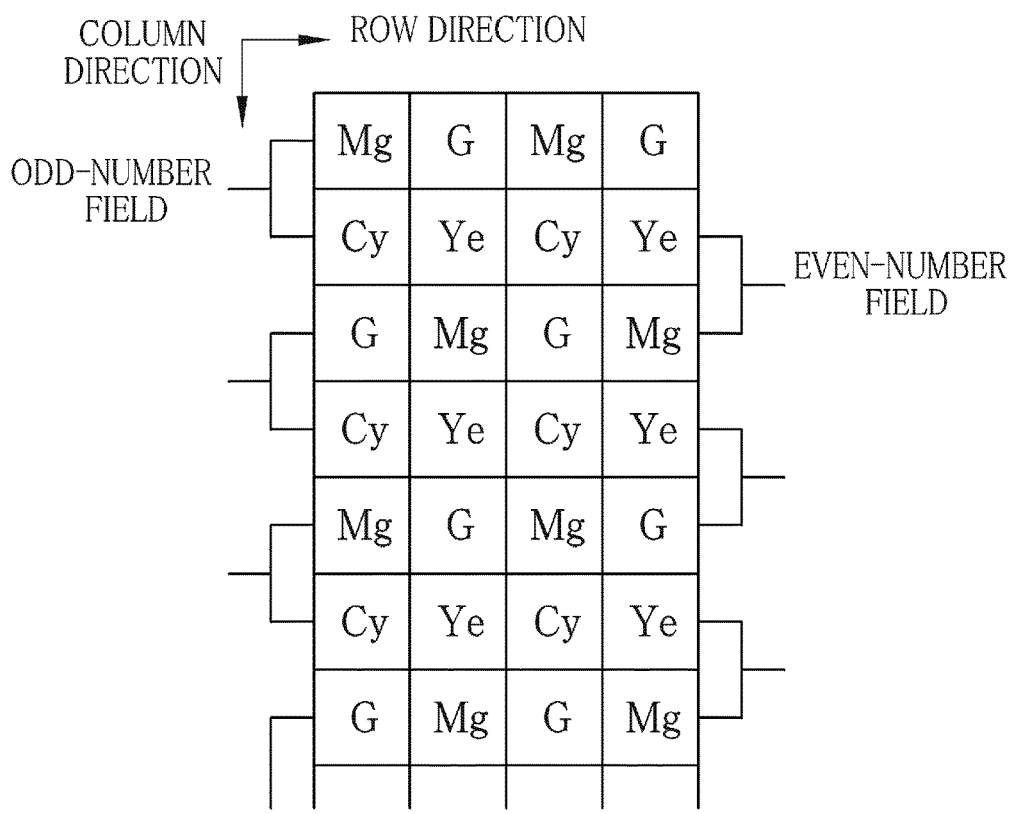
FIG. 19 is a schematic view of a modification example of the complementary color type color separation filter.

Each of the above embodiments uses the complementary color type imaging device 28 having the complementary color type color separation filter 28$a$ of the complementary-color checkered-pattern color-difference line sequential method, as shown in FIG. 7, but may use another complementary color type imaging device having another complementary color type color separation filter, as shown in FIG. 19, of the complementary-color checkered-pattern color-difference line sequential method, instead.

In each of the above embodiments, the combination of the Mg pixel and the Cy pixel composes the first mixed pixel, and the combination of the G pixel and the Ye pixel composes the second mixed pixel, and the combination of the Mg pixel and the Ye pixel composes the third mixed pixel, and the combination of the G pixel and the Cy pixel composes the fourth mixed pixel. However, the combinations of mixed pixels are not limited to these and arbitrarily changeable.

According to each of the above embodiments, the imaging controller 32, the CDS circuit 33, the A/D converter 34, and the like are contained in the processor device 12, but may be provided in the endoscope 13.

According to each of the above embodiments, both of the complementary color type endoscope and the primary color type endoscope are connectable to the light source device and the processor device, but only the complementary color type endoscope may be connectable thereto.

In each of the above embodiments, the light source device and the processor device are configured as independent devices, but may be formed into a single device. Furthermore, the light source device may be incorporated in the endoscope.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
a light source device for simultaneously producing first and second narrowband light having difference wavelength bands;
an imaging device having a plurality of types of pixels sensing both of said first and second narrowband light, a signal value being read out of each of said plurality of types of pixels; and
a processor configured to:
apply a matrix operation to said signal value to produce first and second display signals D1 and D2; and
correct said first and second display signals D1 and D2 on the basis of the following expression (a):

$$\begin{pmatrix} D1' \\ D2' \end{pmatrix} = \begin{pmatrix} 1 & -K_2 \\ -K_1 & 1 \end{pmatrix} \begin{pmatrix} D1 \\ D2 \end{pmatrix} \quad (a)$$

wherein, $K_1$ is a first correction coefficient representing the ratio of a signal value of said second display signal to a signal value of said first display signal under independent application of only said first narrowband light, and $K_2$ is a second correction coefficient representing the ratio of a signal value of said first display signal to a signal value of said second display signal under independent application of only said second narrowband light.

2. The endoscope system according to claim 1, wherein the processor is further configured to calculate said first and second correction coefficients $K_1$ and $K_2$, on the basis of said signal values of said first and second display signals obtained under independent application of each of said first and second narrowband light from said light source device.

3. The endoscope system according to claim 1, wherein said imaging device is a complementary color type imaging device, and signal values of a plurality of types of mixed pixels are read out of said imaging device; and
said processor is further configured to produce said first and second display signals D1 and D2 by performing said matrix operation of said signal values of said plurality of types of mixed pixels.

4. The endoscope system according to claim 3, wherein said complementary color type imaging device has a matrix of at least four types of pixels for performing photoelectric conversion of light of different colors, and two types of said four types of pixels next to in a vertical scan direction compose a first mixed pixel, and other two types of said four types of pixels next to in said vertical scan direction compose a second mixed pixel.

5. The endoscope system according to claim 4, wherein
each of said four types of pixels has one of color filter segments of cyan, magenta, yellow, and green arranged in a checkered pattern;
said plurality of types of mixed pixels include said first mixed pixel being a combination of a magenta pixel and a cyan pixel, and said second mixed pixel being a combination of a green pixel and a yellow pixel; and
said first narrowband light has a center wavelength in a blue or violet wavelength range, and said second narrowband light has a center wavelength in a green wavelength range.

6. The endoscope system according to claim 5, wherein said processor is further configured to perform said matrix operation so as to make a signal of said first mixed pixel as a main signal of said first display signal D1 and make a signal of said second mixed pixel as a main signal of said second display signal D2.

7. The endoscope system according to claim 3, wherein a complementary color type endoscope having said complementary color type imaging device and a primary color type endoscope having a primary color type imaging device are detachably connected to said light source device.

8. The endoscope system according to claim 7, wherein
each of said complementary color type endoscope and said primary color type endoscope has information storage for storing specific information; and
said endoscope system includes a controller for reading out said specific information from said information storage of said complementary color type endoscope or said primary color type endoscope that is connected to said light source device, in order to judge the type of said connected endoscope.

9. The endoscope system according to claim 8, wherein
said information storage stores said first and second correction coefficients $K_1$ and $K_2$; and
upon connecting said complementary color type endoscope or said primary color type endoscope to said light source device, said controller reads out said first and second correction coefficients $K_1$ and $K_2$ from said information storage, and enters said first and second correction coefficients $K_1$ and $K_2$ into said processor.

10. An endoscope system comprising:
a light source device for simultaneously producing first and second narrowband light having difference wavelength bands;
an imaging device having a plurality of types of pixels sensing both of said first and second narrowband light, a signal value being read out of each of said plurality of types of pixels; and
a processor configured to:
apply a matrix operation to said signal value to produce first and second display signals D1 and D2; and
correct said first and second display signals D1 and D2 on the basis of the following expression (b):

$$\begin{pmatrix} D1' \\ D2' \end{pmatrix} = \begin{pmatrix} 1 & R_1 \\ R_2 & 1 \end{pmatrix} \begin{pmatrix} 1 & -K_2 \\ -K_1 & 1 \end{pmatrix} \begin{pmatrix} D1 \\ D2 \end{pmatrix} \quad (b)$$

wherein, $K_1$ is a first correction coefficient representing the ratio of a signal value of said second display signal to a signal value of said first display signal under independent application of only said first narrowband light, and $K_2$ is a second correction coefficient representing the ratio of a signal value of said first display signal to a signal value of said second display signal under independent application of only said second narrowband light, and $R_1$ is a first color mixture rate representing the rate of a second narrowband light component within a corrected first display signal D1', and R2 is a second color mixture rate representing the rate of a first narrowband light component within a corrected second display signal D2'.

11. The endoscope system according to claim 10, wherein
a complementary color type endoscope having a complementary color type imaging device as said imaging device and a primary color type endoscope having a primary color type imaging device as said imaging device are detachably connected to said light source device;
each of said complementary color type endoscope and said primary color type endoscope includes information storage for storing said first and second color mixture rates $R_1$ and $R_2$; and
said endoscope system includes a controller for reading out said first and second color mixture rates $R_1$ and $R_2$ from said information storage and entering said first and second color mixture rates $R_1$ and $R_2$ into said mixed color corrector, upon connecting said complementary color type endoscope or said primary color type endoscope to said light source device.

12. The endoscope system according to claim 11, further comprising:
a structure enhancement processor for applying blood vessel enhancement processing to an image produced based on said corrected first and second display signals D1' and D2', wherein
said structure enhancement processor increases the degree of enhancement of a superficial blood vessel with increase in said first color mixture rate $R_1$.

13. An operating method of an endoscope system comprising the steps of:
simultaneously producing first and second narrowband light having difference wavelength bands from a light source device;
outputting a signal value from each of a plurality of types of pixels of an imaging device, each of said pixels sensing both of said first and second narrowband light;
applying a matrix operation to said signal value and producing first and second display signals D1 and D2 by a processor; and
correcting said first and second display signals D1 and D2 by the processor on the basis of the following expression (c):

$$\begin{pmatrix} D1' \\ D2' \end{pmatrix} = \begin{pmatrix} 1 & -K_2 \\ -K_1 & 1 \end{pmatrix} \begin{pmatrix} D1 \\ D2 \end{pmatrix} \quad (c)$$

wherein, $K_1$ is a first correction coefficient representing the ratio of a signal value of said second display signal to a signal value of said first display signal under independent application of only said first narrowband light, and $K_2$ is a second correction coefficient representing the ratio of a signal value of said first display signal to a signal value of said second display signal under independent application of only said second narrowband light.

\* \* \* \* \*